(12) United States Patent
Franzen et al.

(10) Patent No.: US 9,102,634 B2
(45) Date of Patent: Aug. 11, 2015

(54) PROCESS FOR THE PREPARATION OF (1S,4R)-2-OXA-3-AZABICYCLO[2,2.1]HEPT-5-ENES

(76) Inventors: Manuela Franzen, Morel (CH); Christian Noti, Glis (CH)

( * ) Notice: Subject to any disclaimer, the term of this patent is extended or adjusted under 35 U.S.C. 154(b) by 0 days.

(21) Appl. No.: 13/392,947

(22) PCT Filed: Aug. 25, 2010

(86) PCT No.: PCT/EP2010/005199
§ 371 (c)(1),
(2), (4) Date: Feb. 28, 2012

(87) PCT Pub. No.: WO2011/023374
PCT Pub. Date: Mar. 3, 2011

(65) Prior Publication Data
US 2012/0157671 A1 Jun. 21, 2012

(30) Foreign Application Priority Data
Aug. 31, 2009 (EP) ..................... 09011146

(51) Int. Cl.
C07D 261/20 (2006.01)
C07H 1/00 (2006.01)
C07D 265/34 (2006.01)

(52) U.S. Cl.
CPC .................... C07D 265/34 (2013.01)

(58) Field of Classification Search
USPC .................. 536/27.1, 55.3; 548/241
See application file for complete search history.

(56) References Cited

FOREIGN PATENT DOCUMENTS

EP 0322242 A2 6/1989
EP 0658539 A1 6/1995

OTHER PUBLICATIONS

Defoin et al, Synthesis, 2000, 12, 1719-26.*
Hall et al, Chem. Comm. 1998, 2251-51.*
Meuwly et al, Helvetica Chimica Acta 1984, 67, pp. 1568-1571.*
Carey et al, Advanced Organic Chemistry, Part B, 3rd Edn, 1990, pp. 236-237.*
Zhang et al, J. Org. Chem. 1998, 63, 885-88.*
Adrian Hall; Patrick D. Bailey; Richard H. Wightman; David C. Rees, Asymmetric Cycloadditions of dienes to chloronitroso compounds derived from carbohydrate ketones: synthesis of (−)-physoperuvine and (+)-epibatidine, Chem. Commun., 1998, pp. 2251, vol. 20.
Albert Defoin; Muriel Joubert; Jean-Marc Heuchel; Christiane Strehler; Jaques Streith , Enantioselective Diels-Alder Reaction with an a-Chloronitroso Dienophile Derived from 5-O-Acetyl-2,3-isopropylidenedioxy-D-ribose, Synthesis, 2000, Schemes 1-4, vol. 12.
Deyi Zhang; Carsten Suling; Marvin J. Miller, The Hetero Diels-Alder Reactions between d-Mannose-Derived Halonitroso Compounds and Cyclopentadiene: Scope and Limitation, J. Org. Chem., 1998, pp. 885-888, Scheme 1, compound 4, vol. 63, No. 3.
Le Camus et al., Stereoselective Synthesis of 5-Methylphosphono-D-Arabino Hydroximolactone, Inhibitor of Glucosamine-6-Phosphate Synthase and Phosphoglucose Isomerase, Tetrahedron Letters, Elsevier, Jan. 15, 1998, pp. 287-pp. 288, vol. (97)10514-7, Amsterdam, NL.
Roger Meuwly; Andrea Vasella, , Helvetica Chimica Acta, 1984, pp. 1568-1571, vol. 67.
Heinz Braun; Helena Felber; Gunter Kresze; Franz P. Scmidtchen; Roland Prewo; Andrea Vasella, Diastereoslektive Diels-Alder-Reaktionen mit-Chlornitrososacchariden, Liebigs Annalen Der Chemie, 1993, Compound 2, vol. 1993, No. 2.
Abischer Bernard et al., Deoxynitrosugars. Part 2. Synthesis of protected 1-deoxy-1-nitroaldoses, Helvitica Chimica Acta, May 5, 1982, pp. 621-634, vol. 65, No. 3, Basel, CH.

* cited by examiner

*Primary Examiner* — Ganapathy Krishnan
(74) *Attorney, Agent, or Firm* — Gianna Julian-Arnold; Saul Ewing LLP

(57) ABSTRACT

Enantiomerically enriched (1 S,4R)-2-oxa-3-azabicyclo [2.2.1]hept-5-ene of formula wherein PG1 is an amino-protective group, are prepared from cyclopentadiene via hetero-Diels-Alder cycloaddition with protected 1-C-nitroso-β-D-ribofuranosyl halides of formula wherein X is a halogen atom selected from fluorine, chlorine, bromine and iodine, PG2 is a hydroxyl-protective group and PG3 is a 1,2-diol-protective group.

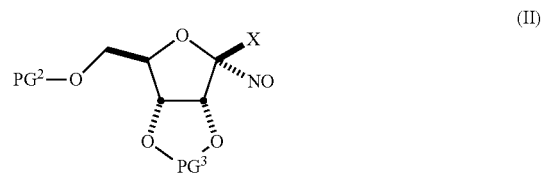

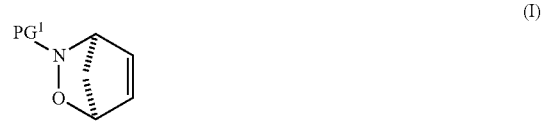

20 Claims, No Drawings

PROCESS FOR THE PREPARATION OF (1S,4R)-2-OXA-3-AZABICYCLO[2.2.1]HEPT-5-ENES

CROSS REFERENCE TO RELATED APPLICATIONS

This application claims the priority of PCT/EP2010/005199, filed on Aug. 25, 2010, which claims the benefit of priority to European Application No. 09011146.9, filed on Aug. 31, 2009, the entire contents of which are hereby incorporated in total by reference.

FIELD OF THE INVENTION

The invention relates to a process for the preparation of enantiomerically enriched (1S,4R)-2-oxa-3-azabicyclo[2.2.1]hept-5-enes of formula

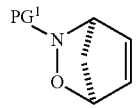

(I)

wherein $PG^1$ is an amino-protective group.

It further relates to novel 5-O-protected (1S,4R)-3-(1-C-halo-α-D-ribofuranosyl)-2-oxa-3-azabicyclo[2.2.1]hept-5-enes of formula

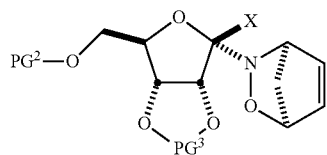

(III)

wherein X is a halogen atom selected from fluorine, chlorine, bromine and iodine, $PG^2$ is a hydroxyl-protective group and $PG^3$ is a 1,2-diol-protective group.

BACKGROUND OF THE INVENTION

N-Protected 2-oxa-3-azabicyclo[2.2.1]hept-5-enes are valuable intermediates in the synthesis of various pharmaceutically active ingredients. See e.g. EP-A-0 322 242 and EP-A-0 658 539 for the N-benzyloxycarbonyl derivative. While some racemic compounds are relatively easily obtainable by hetero-Diels-Alder cycloaddition of nitroso compounds such as benzyl nitrosoformate (obtainable from benzyl N-hydroxycarbamate by oxidation, e.g. with periodate) with cyclopentadiene, a commercially feasible method for the production of the enantiopure or enantiomerically enriched compounds with a wide variety of possible protective groups has not been available.

SUMMARY OF THE INVENTION

It is therefore an objective of the present invention to provide a method for the production of enantiomerically enriched N-protected (1S,4R)-2-oxa-3-azabicyclo[2.2.1]-hept-5-enes that uses commercially available or at least easily accessible starting materials and allows the synthesis of compounds with various protective groups.

It has been found that enantiomerically enriched (1S,4R)-2-oxa-3-azabicyclo[2.2.1]-hept-5-enes of formula

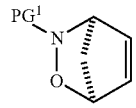

(I)

wherein $PG^1$ is an amino-protective group, can be prepared by a method comprising the steps of
(i) reacting a protected 1-C-nitroso-β-D-ribofuranosyl halide of formula

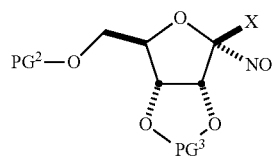

(II)

wherein
X is a halogen atom selected from fluorine, chlorine, bromine and iodine,
$PG^2$ is a hydroxyl-protective group, and
$PG^3$ is a 1,2-diol-protective group,
with cyclopentadiene to obtain a (1S,4R)-3-(1-C-halo-α-D-ribofuranosyl)-2-oxa-3-azabicyclo[2.2.1]hept-5-ene of formula

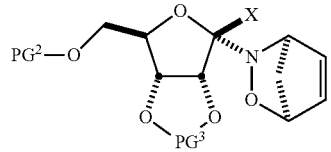

(III)

wherein X, $PG^2$ and $PG^3$ are as defined above;
(ii) hydrolyzing the compound obtained in step (i) to obtain free (1S,4R)-2-oxa-3-azabicyclo[2.2.1]hept-5-ene (I; $PG^1$=H) or the corresponding hydrohalide and the corresponding protected D-ribonolactone; and
(iii) introducing the amino-protective group $PG^1$.

This finding is quite surprising since it had been found that a structurally related xylose-derived α-chloronitroso compound underwent hetero-Diels-Alder cycloadditions with both 1,3-cyclohexadiene and 1,3-cycloheptadiene, but failed to give any cycloaddition product with cyclopentadiene (A. Hall et al., Chem. Commun. 1998, 2251-2252).

Suitable amino-protective groups $PG^1$ are in particular groups forming a carbamate moiety with the amino nitrogen, such as simple alkoxycarbonyl groups, in particular methoxy-, ethoxy- or tert-butoxycarbonyl groups, or substituted methoxycarbonyl groups such as benzyloxycarbonyl (phenylmethoxycarbonyl) or (9-fluorenylmethoxy)carbonyl groups, wherein the phenyl or fluorenyl part may optionally be substituted with one or more alkyl groups or halogen atoms. Such carbamate-forming protective groups are easily introduced by reacting the unprotected amino compound with the respective chloroformate. Other possible amino-protective groups are acyl groups such as acetyl or benzoyl groups which can be introduced by reacting the unprotected amino compound with the respective acyl chloride or anhydride, or benzyl groups which can be introduced by reacting the unprotected amino compound with benzyl chloride or bromide. Acetyl groups may also be introduced by reacting the unprotected amino compound with ketene.

The most preferred amino protective group $PG^1$ is the benzyloxycarbonyl group which can be introduced by reacting the unprotected amino compound with benzyl chloroformate.

The hydroxyl-protective group $PG^2$ may be any group that is not cleaved under the conditions of the process of the invention or during the synthesis of the nitrosoribofuranosyl halide (II). Since the process of the invention does not comprise the cleavage of $PG^2$, it is not necessary that $PG^2$ can be cleaved easily and/or selectively. Suitable hydroxyl-protective groups are those forming an ether (including silyl ether) or ester (including esters of carboxylic acids, carbonic acid, sulfonic acids and alkyl- or arylcarbamic acids) moiety with the hydroxy group at C-5 of the ribose molecule. Ethers may be alkyl ethers, such as methyl or substituted methyl (e.g., methoxymethyl, benzyloxymethyl or triphenylmethyl) ethers, or silyl ethers, such as trialkylsilyl (e.g. trimethylsilyl, triethylsilyl or triisopropylsilyl)ethers. Esters may, for example, be those of simple alkanoic or arenecarboxylic acids, such as acetate or benzoate, of alkane- or arenesulfonic acids, such as methanesulfonate (mesylate) or p-toluenesulfonate (tosylate), or of N-arylcarbamic acids, such as N-phenylcarbamate. These and other protective groups and suitable methods for their introduction are either known to a skilled person or can be found in well-known textbooks and monographs, such as *Greene's Protective Groups in Organic Synthesis* by Peter G. M. Wuts and Theodora W. Greene, John Wiley & Sons, Hoboken, N.J.

A particularly preferred hydroxyl-protective group $PG^2$ is the triphenylmethyl (trityl) group which may have one or more substituents such as $C_{1-4}$ alkyl groups or halogen atoms at its phenyl groups.

Suitable 1,2-diol-protective groups include aldehyde- and ketone-derived groups which, together with the oxygen atoms (O-2 and O-3) and the adjacent carbon atoms (C-2 and C-3) form a cyclic acetal or ketal. Such protective groups can be introduced by either directly reacting the unprotected diol with an aliphatic or aromatic aldehyde or an aliphatic, cycloaliphatic or aromatic ketone, or via trans-acetalization or trans-ketalization using a suitable open-chain acetal or ketal, such as dimethoxymethane or 2,2-dimethoxypropane. These (trans-) acetalization or ketalization reactions are usually acid-catalyzed. Examples of acetal- and ketal-forming 1,2-diol-protective groups are methylene (introduced by reacting with formaldehyde or a formaldehyde acetal), ethylidene (by reacting with acetaldehyde or an acetal thereof), benzylidene (by reacting with benzaldehyde or an acetal thereof), isopropylidene (by reacting with acetone or 2,2-dimethoxypropane), cyclopentylidene (by reacting with cyclopentanone or 1,1-dimethoxycyclopentane) and cyclohexylidene (by reacting with cyclohexanone or 1,1-dimethoxycyclohexane).

Other suitable 1,2-diol-protective groups are those forming a cyclic orthoester or cyclic carbonate. Examples of cyclic orthoester-forming protective groups are methoxy- and ethoxymethylene (by reacting with trimethyl and triethyl orthoformate, respectively) or 1-methoxyethylidene (by reacting with trimethyl orthoacetate or 1,1-dimethoxyethene). A cyclic carbonate group may be introduced by reacting the 1,2-diol with phosgene, diphosgene (trichloromethyl chloroformate) or triphosgene (bis(trichloromethyl) carbonate).

In a particularly preferred embodiment the 1,2-diol-protective group $PG^3$ is isopropylidene ($=C(CH_3)_2$).

In a preferred embodiment, the substituent X is chlorine.

The cycloaddition step (i) is advantageously carried out in an inert solvent such as an aliphatic or aromatic hydrocarbon, a halogenated hydrocarbon, or an open-chain or cyclic ether. Non-limiting examples for such classes of solvents are hexanes, toluene, dichloromethane, tetrahydrofuran, methyl tert-butyl ether, and the like.

The cycloaddition step (i) is advantageously carried out at a temperature between $-100$ and $+40°$ C., preferably between $-80$ and $0°$ C. and most preferably at about $-78°$ C.

The reaction time of the cycloaddition step (i) is typically in the range of a few minutes to about one hour.

In a preferred embodiment the three steps (steps (i) to (iii)) of the process of the invention are carried out without isolating the intermediates (1S,4R)-3-(1-C-halo-α-D-ribofuranosyl)-2-oxa-3-azabicyclo[2.2.1]hept-5-ene of formula III, and/or the unprotected (1S,4R)-2-oxa-3-azabicyclo[2.2.1]hept-5-ene (formula I; $PG^1$=H) or its hydrohalide of formula

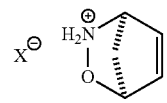

wherein X is as defined above.

In a preferred embodiment the 5-O-protected 1-C-nitroso-β-D-ribofuranosyl halide of formula II used in step (i) has been prepared by reacting the corresponding 5-O-protected D-ribofuranose oxime of formula

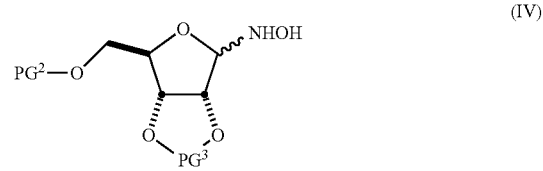

wherein $PG^2$ and $PG^3$ are as defined above, with two equivalents of a hypohalite of formula

wherein X is chlorine, bromine or iodine, n is 1 or 2 and M is selected from the group consisting of alkali metals and alkaline earth metals, i.e., with a hypohalite selected from the group consisting of alkali metal hypohalites and alkaline earth metal hypohalites. The 5-O-protected D-ribofuranose oxime (IV) may also be present in the open-chain aldoxime form or as a mixture of the open-chain and the depicted furanose form. While the prior art syntheses of 5-O-protected 1-C-nitroso-β-D-ribofuranosyl halides and related compounds from the corresponding oximes comprise two steps, namely an oxidation step (e.g. with periodate) to the corresponding oximinolactone and an oxidative halogenation (e.g. with tert-butyl hypochlorite) to the nitrosoribofuranosyl halide, it has been found that the transformation can be achieved in one process step using two equivalents of an inexpensive alkali or alkaline earth metal hypohalite which serves as oxidant and halogenating agent.

Most preferably, the transformation is carried out with sodium hypochlorite as hypohalite.

In another preferred embodiment the 5-O-protected D-ribonolactone of formula

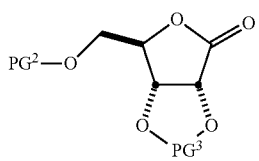

(V)

wherein $PG^2$ and $PG^3$ are as defined above, which is formed in the hydrolysis of the intermediate of formula III, is recovered and reconverted via the oximinolactone into the protected 1-C-nitroso-β-D-ribofuranosyl halide of formula II, e.g. by reducing it to the corresponding protected D-ribofuranose which is then reacted with hydroxylamine to obtain the corresponding oxime of formula IV, which in turn is reacted with hypohalite as described above. When this recycling method is used, the consumption of the chiral auxiliary is minimized and—theoretically—only cyclopentadiene, hydroxylamine, sodium hypochlorite, a suitable reducing agent for the reduction of the lactone, and a source of the amino-protective group $PG^1$ are required in stoichiometric amounts.

The protected (1S,4R)-(1-C-halo-α-D-ribofuranosyl)-2-oxa-3-azabicyclo[2.2.1]hept-5-enes of formula

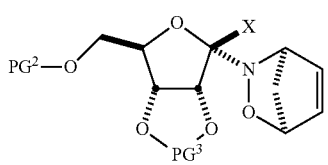

(III)

wherein X, $PG^2$ and $PG^3$ are as defined above are novel and also an object of the invention.

In a preferred embodiment of the (1S,4R)-(1-C-halo-α-D-ribofuranosyl)-2-oxa-3-azabicyclo[2.2.1]hept-5-ene of formula III, X is chlorine.

In another preferred embodiment of the (1S,4R)-(1-C-halo-α-D-ribofuranosyl)-2-oxa-3-azabicyclo[2.2.1]hept-5-ene of formula III, $PG^2$ is a triphenylmethyl group.

In still another preferred embodiment of the (1S,4R)-(1-C-halo-α-D-ribofuranosyl)-2-oxa-3-azabicyclo[2.2.1]hept-5-ene of formula III, $PG^3$ is an isopropylidene group

DETAILED DESCRIPTION OF THE INVENTION

According to the process of the invention it is possible to obtain the desired enantiomerically enriched (1S,4R)-2-oxa-3-azabicyclo[2.2.1]hept-5-enes (I) in an enantiomeric excess (ee) of 80% or more, preferably 90% or more and particularly preferably 95% or more.

EXAMPLES

The following non-limiting examples will illustrate the process of the invention and the preparation of the novel intermediates.

Example 1

2,3-O-Isopropylidene-D-ribofuranose

Concentrated sulfuric acid (0.3 mL) was added to a suspension of D-ribose (12.5 g, 83 mmol) in acetone (125 mL). The reaction mixture was stirred at room temperature for 90 min to obtain a clear solution which was then neutralized with saturated aqueous sodium carbonate. The mixture was filtered over Celite® and concentrated in vacuo.

Yield: 15.7 g (≈100%)

Example 2

2,3-O-Isopropylidene-5-O-trityl-D-ribofuranose 2,3-O-Isopropylidene-D-ribofuranose (15.7 g, 83.1 mmol) was dissolved in pyridine (100 mL) and trityl chloride (27.8 g, 0.1 mol) was added. The mixture was stirred at room temperature for 24 h. The solvent was evaporated and the residue purified by column chromatography on silicagel using hexanes/ethyl acetate (v.v=4:1) as eluant.

Yield: 32.3 g (90%)

Example 3

2,3-O-Isopropylidene-5-O-trityl-D-ribofuranose 2,3-O-Isopropylidene-D-ribofuranose (20 g, 105.2 mmol) was dissolved in dichloromethane (200 mL) at 0° C. Triethylamine (10.9 g, 107.5 mmol) and a catalytic. amount of pyridine were added to the reaction mixture, followed by the addition of trityl chloride (27.8 g, 0.1 mol). The mixture was stirred at 0° C. for 3 h and further 12 h at room temperature. To the reaction mixture was added saturated aqueous sodium bicarbonate (80 mL) and the phases were separated. The organic phase was dried over anhydrous sodium sulfate, filtered, and the solvents were removed in vacuo. The crude product was used without further purification in the next step.

Yield: 38.5 g (85%)

Example 4

2,3-O-Isopropylidene-5-O-trityl-D-ribofuranose oxime (IV; $PG^2$=trityl, $PG^3$==C(CH$_3$)$_2$)

Hydroxylamine hydrochloride (58 g, 0.83 mol) was added to a solution of 2,3-O-isopropylidene-5-O-trityl-D-ribofuranose (30 g, 0.69 mol) in pyridine (200 mL). The mixture was stirred at room temperature for 3 h and then water (250 mL) and dichloromethane (250 mL) were added and the phases were separated. The organic phase was dried over anhydrous sodium sulfate and filtered and the solvent was evaporated. The residue was purified by column chromatography on silicagel using hexanes/ethyl acetate (v.v=7:3) as eluant.

Yield: 25.5 g (82%)

Example 5

2,3-O-Isopropylidene-5-O-trityl-D-ribofuranose oxime (IV; $PG^2$=trityl, $PG^3$==C(CH$_3$)$_2$)

To hydroxylamine hydrochloride (10.9 g, 0.16 mol) in ethanol (150 mL) was added sodium bicarbonate (13.11 g, 0.16 mol). The reaction mixture was stirred at room temperature until the evolution of carbon dioxide ceased. Then 2,3-O-isopropylidene-5-O-trityl-D-ribofuranose (15 g, 0.34 mol), dissolved in ethanol (50 mL), was added and stirring was continued for 2 h. The reaction mixture was then filtered over a plug of silica and ethyl acetate (200 mL) and water (200 mL) were added. The organic phase was dried over anhydrous sodium sulfate and filtered and the solvent was evaporated. The crude product was used without further purification in the next step.

Yield: 13.4 g (86%).

Example 6

2,3-O-Isopropylidene-1-C-nitroso-5-O-trityl-β-D-ribofuranosyl chloride (II, X=Cl, PG$^2$=triphenylmethyl, PG3==C(CH$_3$)$_2$)

Sodium hypochlorite (5 wt. % aqueous solution, 140 mL, 0.92 mol) was added dropwise at 0° C. under stirring to a solution of 2,3-O-isopropylidene-5-O-trityl-D-ribofuranose oxime (25.5 g, 0.57 mol) in dichloromethane (150 mL). After 30 min at 0° C. the reaction mixture was allowed to warm to room temperature and stirred for another 30 min. Water (50 mL) was added and the phases were separated. The organic phase was dried over anhydrous sodium sulfate and filtered. The product was isolated by evaporating the solvent.

Yield: 25 g (88%)

Example 7

(1S,4R)-3-Benzyloxycarbonyl-2-oxa-3-azabicyclo[2.2.1]hept-5-ene (I, PG$^1$==COOCH$_2$C$_6$H$_5$)

2,3-O-Isopropylidene-1-C-nitroso-5-O-trityl-β-D-ribofuranosyl chloride (1 g, 1.96 mmol) was dissolved in toluene or dichloromethane (10 mL). The solution was cooled to −78° C. and cyclopentadiene (1 g, 14.6 mmol) was added within 30 min under stirring. The reaction mixture was stirred at −78° C. for 1 h and the warmed to 0° C. Water (25 mL) was added at 0° C. and the phases were separated. Methyl tert-butyl ether (5 mL), benzyl chloroformate (350 mg, 2.0 mmol) and sodium hydroxide (25 wt. % aqueous solution, 800 mg, 5 mmol) were added and the resulting mixture stirred at room temperature for 30 min. The phases were separated, the organic phase was washed with brine (5 mL), dried over anhydrous sodium sulfate and filtered. The product was isolated by evaporating the solvent.

Yield: 89% ee: 96%

When the reaction with cyclopentadiene was repeated at −20° C. and 0° C., the ee of the product was 88% and 82%, respectively.

The invention claimed is:

1. A process for preparing an enantiomerically enriched (1S,4R)-2-oxa-3-azabicyclo [2.2.1] hept-5-ene of formula

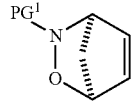

(I)

wherein PG$^1$ is an amino-protective group, the process comprising the steps of
(i) reacting a protected 1-C-nitroso-β-D-ribofuranosyl halide of formula

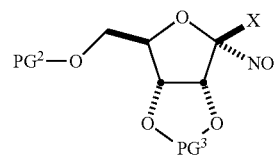

(II)

wherein
X is a halogen atom selected from the group consisting of fluorine, chlorine, bromine and iodine,
PG$^2$ is a hydroxyl-protective group, and
PG$^3$ is selected from the group consisting of methylene, ethylidene, isopropylidene, cyclopentylidene and cyclohexylidene;
with cyclopentadiene to obtain a (1S,4R)-3-(1-C-halo-α-D-ribofuranosyl)-2-oxa-3-azabicyclo[2.2.1]hept-5-ene of formula

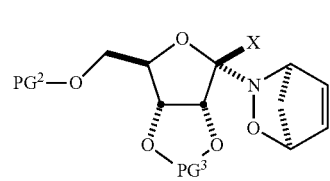

(III)

wherein X, PG$^2$ and PG$^3$ are as defined above;
(ii) hydrolyzing the compound obtained in step (i) to obtain free (1S,4R)-2-oxa-3-azabicyclo[2.2.1]hept-5-ene (I; PG$^1$=H) or the corresponding hydrohalide and the corresponding 5-O-protected D-ribonolactone by phase separation, wherein the enantiomeric excess of (I) or corresponding hydrohalide is at least 80%; and
(iii) introducing the amino-protective group PG$^1$; wherein step (i) is carried out at a temperature between about −80° C. and about 0° C.

2. The process of claim 1 wherein the amino-protective group PG$^1$ is a benzyloxycarbonyl group and is introduced by reacting the (1S,4R)-2-oxa-3-azabicyclo-[2.2.1]hept-5-ene with benzyl chloroformate.

3. The process of claim 1 wherein X is chlorine.

4. The process of claim 1 wherein the 1,2-diol-protective group PG$^3$ is an isopropylidene group.

5. The process of claim 1 wherein the steps (i) to (iii) are carried out without isolating the intermediate of formula III or the free (1S,4R)-2-oxa-3-azabicyclo[2.2.1]hept-5-ene (I; PG$^1$=H) or its hydrohalide.

6. The process of claim 1 wherein the protected 1-C-nitroso-β-D-ribofuranosyl halide of formula II is prepared by reacting the corresponding protected D-ribofuranose hydroxylamine of formula

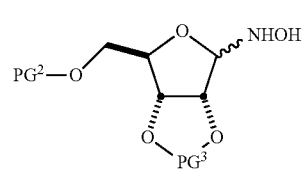

(IV)

with two equivalents of a hypohalite of formula $M^{n+}(OX)_n^-$
wherein X is chlorine, bromine or iodine, n is 1 or 2 and M is selected from the group consisting of alkali metals and alkaline earth metals.

7. The process of claim 6 wherein the hypohalite is sodium hypochlorite.

8. The process of claim 1 wherein the protected D-ribonolactone obtained in step (ii) is recovered and reconverted into the protected 1-C-nitroso-β-D-ribofuranosyl halide (II).

9. The process of claim 1 wherein the hydroxyl-protective group $PG^2$ is a triphenylmethyl group.

10. The process of claim 1, wherein the 1,2-diol-protective group $PG^3$ is a methylene group.

11. A (1S,4R)-3-(1-C-halo-α-D-ribofuranosyl)-2-oxa-3-azabicyclo[2.2.1]hept-5-ene of formula

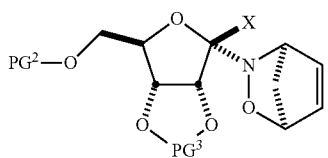

(III)

wherein

X is a halogen atom selected from the group consisting of fluorine, chlorine, bromine and iodine, $PG^2$ is a hydroxyl-protective group, and $PG^3$ is selected from the group consisting of methylene, ethylidene, isopropylidene, cyclopentylidene and cyclohexylidene.

12. The (1S,4R)-3-(1-C-halo-α-D-ribofuranosyl)-2-oxa-3-azabicyclo[2.2.1]hept-5-ene of claim 11 wherein X is chlorine.

13. The (1S,4R)-3-(1-C-halo-α-D-ribefuranosyl)-2-oxa-3-azabicyclo[2.2.1]hept-5-ene of claim 11 wherein $PG^2$ is a triphenylmethyl group.

14. The (1S,4R)-3-(1-C-halo-α-D-ribefuranosyl)-2-oxa-3-azahicyclo[2.2.1]hept-5-ene of claim 11 wherein $PG^3$ is an isopropylidene group.

15. The process of claim 6 wherein the hypobalite is potassium hypochlorite.

16. The process of claim 1 wherein $PG^3$ is an ethylidene group.

17. The process of claim 1 wherein X is bromine.

18. The process of claim 1 wherein X is fluorine.

19. The process of claim 1 wherein $PG^2$ is a trityl group having one or more substituents selected from the group consisting of $C_{1-4}$ alkyl groups and halogen atoms at its phenyl groups.

20. The process of claim 1 wherein the step (i) is carried out at about −78° C.

UNITED STATES PATENT AND TRADEMARK OFFICE
CERTIFICATE OF CORRECTION

PATENT NO. : 9,102,634 B2
APPLICATION NO. : 13/392947
DATED : August 11, 2015
INVENTOR(S) : Manuela Lengen et al.

It is certified that error appears in the above-identified patent and that said Letters Patent is hereby corrected as shown below:

On the title page

Item (54), "PROCESS FOR THE PREPARATION OF (1S,4R)-2-OXA-3-AZABICYCLO[2,2.1]HEPT-5-ENES" should be revised to "PROCESS FOR THE PREPARATION OF (1S,4R)-2-OXA-3-AZABICYCLO[2.2.1] HEPT-5-ENES"
Item (75), "Manuela Franzen" should be "Manuela Lengen"
Item (73), please add assignee data
Assignee: LONZA LTD., Lonzastrasse, Visp, Switzerland 3930

In the specification

Column 6, line 22 - "v.v=4:1" should be "v:v = 4:1"
Column 6, line 55 - "v.v=7:3" should be "v:v = 7:3"
Column 7, lines 14 and 15 - "X═Cl" should be "X = Cl" - "PG3" should be "PG$^3$"

In the claims

Column 9, line 10, Claim 9: "triphenylinethyl" should be "triphenylmethyl"
Column 10, line 3, Claim 11: "cyciopentylidene" should be "cyclopentylidene"
Column 10, line 8 and line 11, Claim 13 and 14: "...ribefuranosyl..." should be "...ribofuranosyl..."

Signed and Sealed this
Second Day of February, 2016

Michelle K. Lee
*Director of the United States Patent and Trademark Office*

UNITED STATES PATENT AND TRADEMARK OFFICE
CERTIFICATE OF CORRECTION

PATENT NO.         : 9,102,634 B2
APPLICATION NO.    : 13/392947
DATED              : August 11, 2015
INVENTOR(S)        : Manuela Lengen et al.

Page 1 of 1

It is certified that error appears in the above-identified patent and that said Letters Patent is hereby corrected as shown below:

On the title page

Item (54), "PROCESS FOR THE PREPARATION OF (1S,4R)-2-OXA-3-AZABICYCLO [2,2.1]HEPT-5-ENES" should be revised to "PROCESS FOR THE PREPARATION OF (1S,4R)-2-OXA-3-AZABICYCLO[2.2.1] HEPT-5-ENES"
Item (75), "Manuela Franzen" should be "Manuela Lengen"
Item (73), please add assignee data
Assignee: LONZA LTD., Lonzastrasse, Visp, Switzerland 3930

In the specification
Column 1, lines 1-3, "PROCESS FOR THE PREPARATION OF (1S,4R)-2-OXA-AZABICYCLO [2,2.1]HEPT-5-ENES" should be revised to "PROCESS FOR THE PREPARATION OF (1S,4R)-2-OXA-3-AZABICYCLO[2.2.1] HEPT-5-ENES".
Column 6, line 22 - "v.v=4:1" should be "v:v = 4:1"
Column 6, line 55 - "v.v=7:3" should be "v:v = 7:3"
Column 7, lines 14 and 15 - "X=Cl" should be "X = Cl" - "PG3" should be "PG$^3$"

In the claims

Column 9, line 10, Claim 9: "triphenylinethyl" should be "triphenylmethyl"
Column 10, line 3, Claim 11: "cyciopentylidene" should be "cyclopentylidene"
Column 10, line 8 and line 11, Claim 13 and 14: "...ribefuranosyl..." should be "...ribofuranosyl..."

This certificate supersedes the Certificate of Correction issued February 2, 2016.

Signed and Sealed this
Twenty-first Day of June, 2016

Michelle K. Lee
*Director of the United States Patent and Trademark Office*